United States Patent [19]
Queisser et al.

[11] Patent Number: 5,818,953
[45] Date of Patent: Oct. 6, 1998

[54] OPTICAL CHARACTERIZATION METHOD

[75] Inventors: Andrew Queisser; Joseph G. LaChapelle, both of Albany, Oreg.; Daniel M. Dionas, Kennewick; Michael P. Minelli, Richland, both of Wash.

[73] Assignee: Lamb-Weston, Inc., Richland, Wash.

[21] Appl. No.: 634,093

[22] Filed: Apr. 17, 1996

[51] Int. Cl.$^6$ ........................................... G06K 9/00
[52] U.S. Cl. ..................... 382/110; 382/165; 209/580; 348/89; 356/406
[58] Field of Search .................. 209/580–582, 209/586, 938, 939; 345/154; 348/86, 89, 582; 356/405, 406, 518, 520; 358/523; 364/526; 382/110, 162, 165; 395/131

[56] References Cited

U.S. PATENT DOCUMENTS

| | | | |
|---|---|---|---|
| 4,747,148 | 5/1988 | Watanabe et al. | 382/141 |
| 5,206,918 | 4/1993 | Levene | 382/110 |
| 5,659,624 | 8/1997 | Fazzari et al. | 382/110 |

OTHER PUBLICATIONS

Lebégue et al., "Fusion of Color and Geometric Information," pp. 219–223.

United States Department of Agriculture, "Color Standards for Frozen French Fried Potatoes," 4th Ed., 1988, Munsell Color, Baltimore, Maryland 64–1, 2 pages.

"AccuScan Quality Control Monitor, Ultra Fidelity Color System Sets World Standrad in Food Processing SPC/SQC," Key Technology, Inc. brochure, 8 pages, 1992.

"ColorSort II, A Profile in Productivity," Key Technology, Inc. brochure, 8 pages, 1993.

*Primary Examiner*—Joseph Mancuso
*Assistant Examiner*—Marc Bobys
*Attorney, Agent, or Firm*—Klarquist Sparkman Campbell Leigh & Whinston, LLP

[57] ABSTRACT

This invention includes an optical characterization method capable of determining various characteristics of samples that preferably include naturally-occurring color deviations. In the preferred embodiment, this method is used in connection with food products and, particularly, potato products such as french fried potatoes. The method of this invention overcomes such disadvantages by generating from the RGB pixel values a sample-based color space that corresponds to the naturally-occurring color deviations of the samples. Preferably, the method includes generating HSI pixel values that correspond to the RGB pixel values and are defined with respect to an HSI color space having hue, saturation, and intensity coordinates. The sample-based representation of the color characteristics of the samples is determined on a pixel-by-pixel basis. As a result, color grades for the samples can be assigned according to the distribution of pixels within the sample-based representation. Moreover, defects or color variation, as well as the length distribution of the samples, may also be determined.

1 Claim, 9 Drawing Sheets

OPTICAL CHARACTERIZATION METHOD

TECHNICAL FIELD

The present invention relates to optical characterization methods and, in particular, to a method of grading samples with respect to a sample-based color space.

BACKGROUND OF THE INVENTION

Color grading is used widely to characterize various products having naturally-occurring color variations, such as raw and processed food products. With respect to food products such as french fried potatoes, for example, color grading has been performed manually by human observers and automatically by optical characterization systems.

In manual color grading of french fried potatoes, for example, human observers compare the predominant colors of a sample of french fried potatoes to a printed chart showing in color french fried potatoes that define particular color grades. One such printed grading chart is promulgated by the United States Department of Agriculture (USDA) as color standard 000-4 for frozen french fried potatoes.

The USDA color standard 000-4 establishes seven standard color grades (000, 00, 0, 1, 2, 3, and 4) according to the degree of browning that predominates a sample. Browning refers to the color change that raw or parfried potato strips undergo when fried and is related to various characteristics of the potato strips as well the frying process. By industry practice, the color grades range in integer steps from grade 000 to grade 0 and in quarter-step grades between the standard grades of 0 and 4. As examples, grade 000 corresponds to french fried potatoes with virtually no browning or other color change, grade ½ corresponds to a generally golden color with little pronounced browning, and grade 4 corresponds to a generally brown color and nearly complete browning of a sample.

Manual grading suffers from several disadvantages. Human visual perception has heightened acuity directed to optical differences. Manual color grading requires an observer to determine absolute color correlation, which only indirectly utilizes the optical differential capability of human perception. Accordingly, manual color grading requires capabilities to which human visual perception is physiologically ill-suited.

Moreover, human visual perception is inherently subjective. Different observers frequently reach different color grading conclusions with respect to identical samples. As a consequence, product consistency can be extremely difficult to obtain with manual grading by different human observers.

To overcome shortcomings of manual optical inspection of products, such as french fried potatoes, a food product optical characterization system was developed and is available as the Agtron® characterization system from Agtron, Inc. of Reno Nev. The Agtron® characterization system is a special application abridged spectrophotometer that determines the ratio of average reflectance of near infrared and green light from a sample. The system has been used to characterize a sample of raw or parfried french fried potatoes. The sample includes multiple french fries packed in a 4 mm deep inspection container or cup during the optical characterization process.

The Agtron® characterization system provides greater consistency in determining average sample color than is available from manual optical inspection. However, the Agtron® characterization system also suffers from several disadvantages. By measuring the average reflectance of all the french fried potato strips in a sample, the Agtron® system requires that only uniformly "average" potato strips be included in a sample. Accordingly, a technician manually identifies and removes from the sample potato strips having defects or color variation from the overall or predominant color of the sample by more than ½ unit on the USDA color standard of 000 to 4. Such manual sorting introduces into the operation of the Agtron® system some of the inconsistency inherent in manual inspection processes. Moreover, removing certain french fries from an otherwise random sample decreases the statistical significance of the sample.

Another disadvantage of the Agtron® system is that it is incapable of determining characteristics of samples other than average reflectance. Most products include other characteristics that could be graded optically, including the number and sizes of defects or color variations and the sizes or lengths of the products. For french fried potatoes, such determinations currently are made manually by human observers or with other dedicated systems.

SUMMARY OF THE INVENTION

This invention includes an optical characterization method capable of determining various characteristics of samples that preferably include naturally-occurring color deviations. In the preferred embodiment, this method is used in connection with food products and, particularly, potato products such as french fried potatoes. The invention is used in connection with an optical grading system having an optical station for obtaining optical data relating to optical characteristics of a selected sample and a computer system for controlling the inspection system and processing the optical data.

The inspection station includes an inspection video camera that images and generates a conventional pixelated RGB video signal corresponding to red, green, and blue color components of the selected sample. The computer system converts the RGB video signal to digitized RGB pixel values in a conventional manner.

The RGB pixel values provide an optical characterization of the sample with respect to a three-dimensional RGB color space. Many automated optical systems characterize samples within the RGB color space, but such characterizations are relatively complex because the RGB color space typically has a poor correlation to sample characteristics of interest.

In particular, sample characteristics of interest are distributed over the RGB color space with a high standard deviation and a high cross correlation. Characteristics of samples with naturally-occurring color deviations form complex, disjointed regions in RGB color space. A major difficulty in such conventional systems, therefore, is to construct RGB models that correspond to selected characteristics.

The method of this invention overcomes such disadvantages by generating from the RGB pixel values a sample-based color space that corresponds to the naturally-occurring color deviations of the samples. Preferably, the method includes generating HSI pixel values that correspond to the RGB pixel values and are defined with respect to an HSI color space having hue, saturation, and intensity coordinates. An aspect of many naturally-occurring color deviations, particularly in food products such as french fried potatoes, is that the predominant naturally-occurring colors frequently have a substantially common hue. The substantially common hue of the predominant colors of the samples is identified from the HSI pixel values, and a sample-based representation of the samples is generated with reference to the substantially common hue.

The sample-based representation of the color characteristics of the samples is determined on a pixel-by-pixel basis. As a result, color grades for the samples can be assigned according to the distribution of pixels within the sample-based representation. Moreover, defects or deviations, as well as average lengths of the samples, may also be determined.

Another aspect of this invention is that this grading method can be utilized to quantify the effects of various manufacturing changes on the grades or other characteristics of products. With reference to the manufacture or processing of french fried potatoes, for example, any of a number of conventional processing steps such as washing, slicing, blanching, parfrying, freezing, and final frying can be varied. Quantifying the optical characteristics of samples subjected to different processing conditions allows the effects of the different processing conditions to be controlled to provide improved products.

The foregoing and other features and advantages of preferred embodiments of the present invention will be more readily apparent from the following detailed description, which proceeds with reference to the accompanying drawings.

DETAILED DESCRIPTION OF PREFERRED EMBODIMENTS

Figure 1:
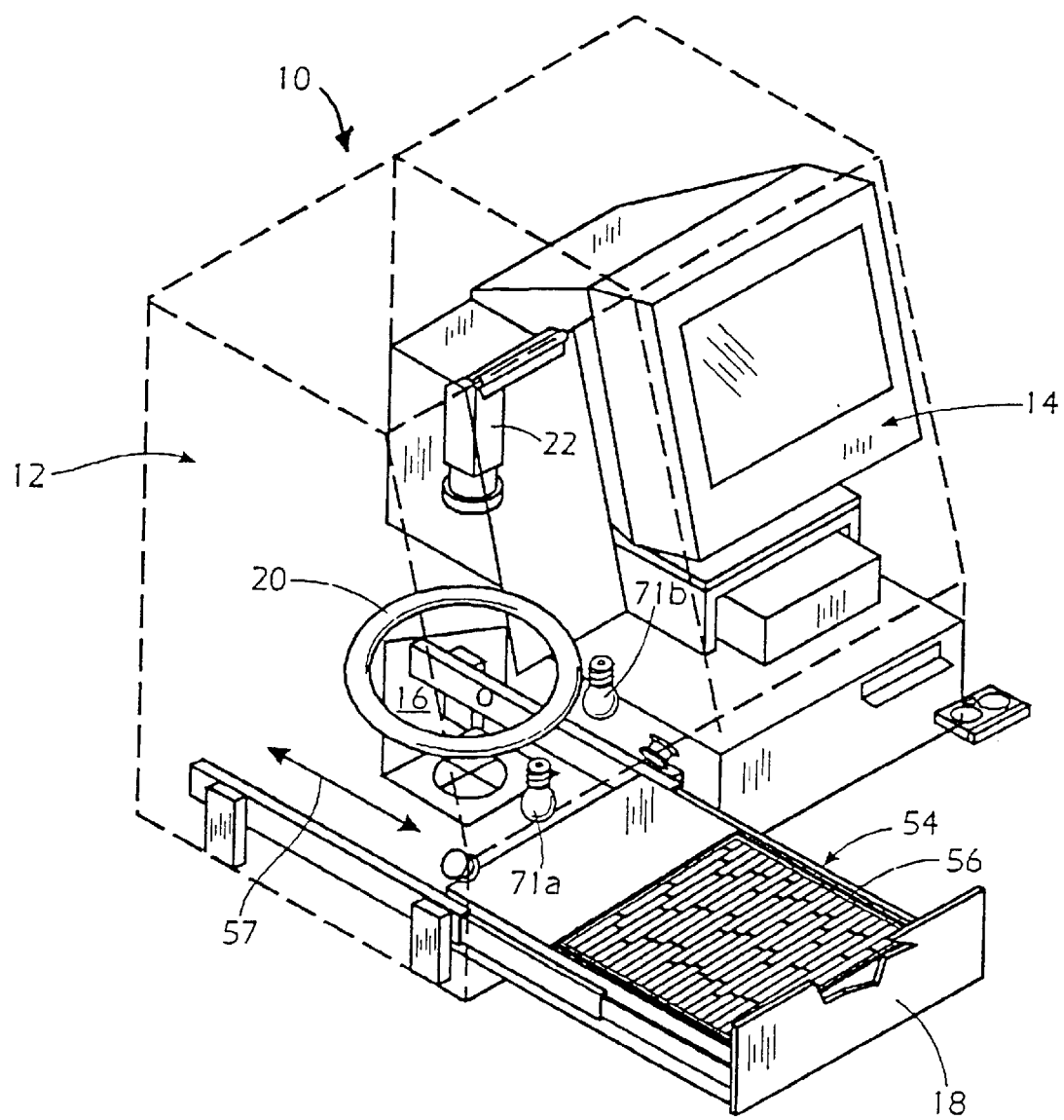
FIG. 1 is a diagrammatic view of an optical grading system that provides an operating environment for the present invention.

FIG. 1 is a diagrammatic view of an optical grading system 10 that provides an operating environment for the preferred embodiment of the present invention. Optical grading system 10 includes an inspection station 12 that obtains optical data relating to optical characteristics of a selected sample (not shown), and a computer system 14 that controls inspection station 12 and processes the optical data according to this invention. Inspection station 12 and computer system 14 are shown relative to an outline of a housing for grading system 10.

In the preferred embodiment described below, the selected sample includes food products that include potatoes, particularly french fried potatoes. The present invention is similarly applicable to other types of samples having naturally-occurring color variations such as processed and raw foods, as well as non-food items.

Inspection station 12 includes an inspection chamber 16 into which the selected samples are carried on a drawer 18 (shown in outline in its open position). Selected samples on drawer 18 in its closed position are illuminated by a ring-shaped light source 20. An inspection video camera 22 images and generates a pixelated RGB video signal corresponding to the selected samples. The RGB video signal represents the samples by red, green, and blue color component signals. Video camera 22 delivers the RGB signal to computer system 14 for processing according to this invention.

Preferably, ring light source 20 is a fluorescent light that generates a cool white or daylight spectrum. Video camera 22 preferably is a full color area scan camera having three area scan photoelectric elements (e.g., CCDs), such as a Model No. XC-003 camera with a 6 mm lens from Sony Corporation.

Figure 2:
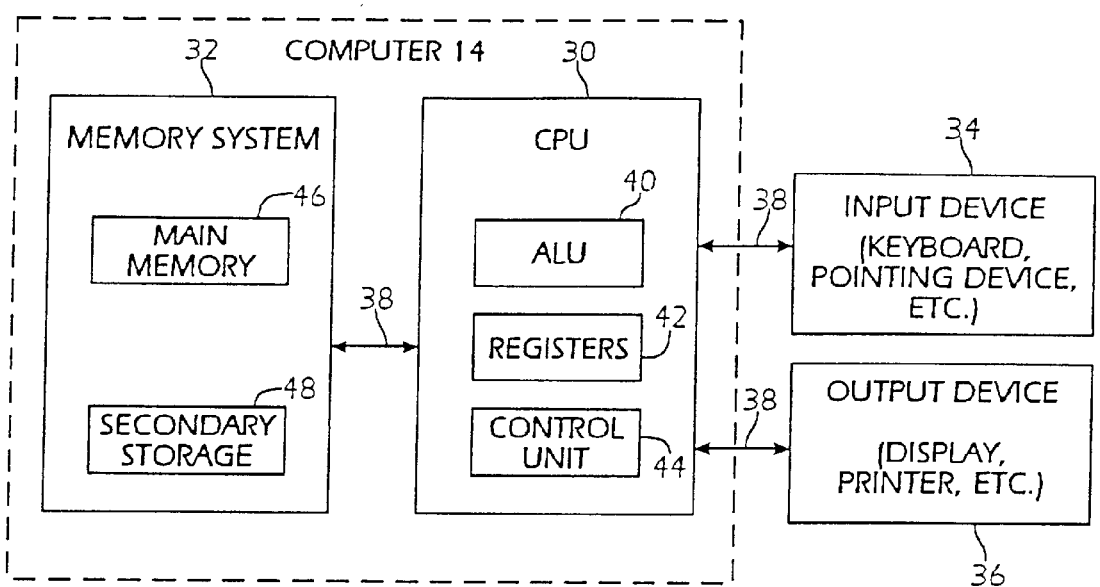
FIG. 2 is a simplified block diagram of a general-purpose computer system employed in the optical grading system of FIG. 1.

FIG. 2 is a simplified block diagram of general-purpose computer system 14, which comprises at least one high speed processing unit (CPU) 30, in conjunction with a memory system 32, an input device 34, and an output device 36. These elements are interconnected by a bus structure 38.

The illustrated CPU 30 is of familiar design and includes an ALU 40 for performing computations, a collection of registers 42 for temporary storage of data and instructions, and a control unit 44 for controlling operation of the system 14. CPU 30 may be a processor having any of a variety of architectures including Alpha from Digital, MIPS from MIPS Technology, NEC, IDT, Siemens, and others, x86 from Intel and others, including Cyrix, AMD, and Nexgen, and the PowerPC from IBM and Motorola.

The memory system 32 includes main memory 46 and secondary storage 48. Illustrated main memory 46 preferably takes the form of 16 megabytes of semiconductor RAM memory. Secondary storage 48 preferably takes the form of long term storage, such as ROM, optical or magnetic disks, flash memory, or tape. Those skilled in the art will appreciate that memory system 32 may comprise many other alternative components.

The input and output devices 34, 36 are also familiar. The input device 34 can comprise a keyboard, a mouse, a physical transducer (e.g. a microphone), etc. The output device 36 can comprise a display, a printer, a transducer (e.g. a speaker), etc. Some devices, such as a network interface or a modem, can be used as input and/or output devices.

As is familiar to those skilled in the art, the computer system 14 further includes an operating system and at least one application program. The operating system is the set of software which controls the operation of computer system 14 and the allocation of resources. The application program is the set of software that performs a task desired by the user, such as the present invention, making use of computer resources made available through the operating system. Both are resident in the illustrated memory system 32.

In accordance with the practices of persons skilled in the art of computer programming, the present invention is described below with reference to symbolic representations of operations that are performed by computer system 14, unless indicated otherwise. Such operations are sometimes referred to as being computer-executed.

It will be appreciated that the operations which are symbolically represented include the manipulation by CPU 30 of electrical signals representing data bits and the maintenance of data bits at memory locations in memory system 32, as well as other processing of signals. The memory locations where data bits are maintained are physical locations that have particular electrical, magnetic, or optical properties corresponding to the data bits.

Figure 3:
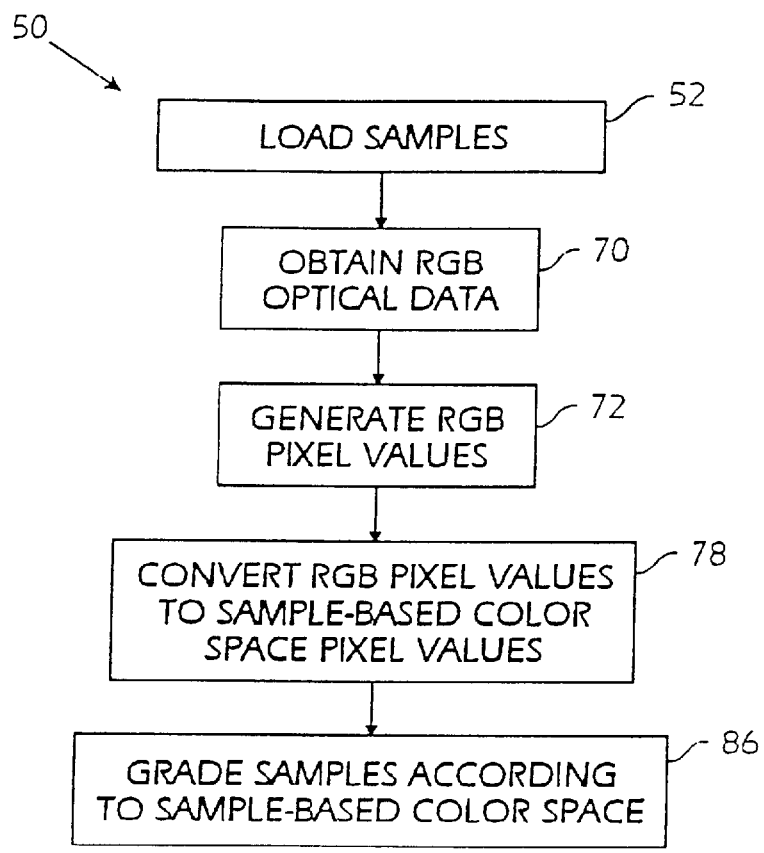
FIG. 3 is a generalized flow diagram of an optical characterization method of the present invention.

FIG. 3 is a generalized flow diagram of an optical characterization method 50 of the present invention. With reference to a preferred embodiment, optical characterization method 50 determines for a sample of multiple french fried potatoes characteristics that include color grade, defects, and length. As a result, preferred optical characterization method 50 determines the major optical characteristics of a sample of french fried potatoes.

Referring to FIGS. 1 and 3, process block 52 indicates that a sample 54 of french fried potatoes is positioned on an inspection tray 56 in drawer 18 and inserted into inspection chamber 16. As is common, the french fried potatoes of sample 54 have elongated configurations. The french fried potatoes of sample 54 preferably are aligned transverse, preferably perpendicular to, an alignment axis 57 and are arranged on inspection tray 56 in a non-contacting and non-overlapping relationship with each other. Contacting and overlapping relationships between the french fried potatoes are, however, acceptable. The orientation of the french fried potatoes preferably is perpendicular to the horizontal line scan direction of camera 22 to maximize imaging resolution and accuracy.

Figure 4A:
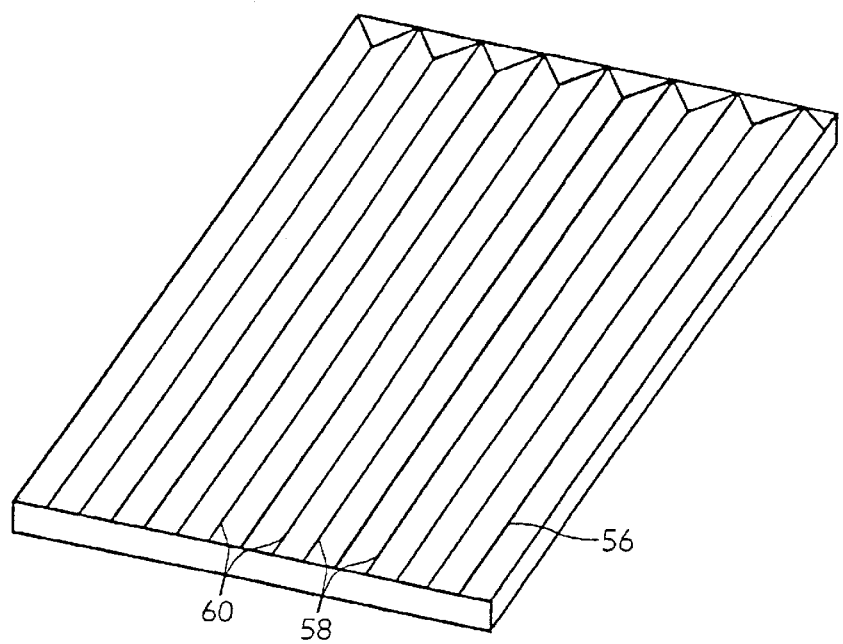
FIGS. 4A and 4B are respective isometric and sectional end views of an inspection tray used in the optical grading system of FIG. 1.
Figure 4B:
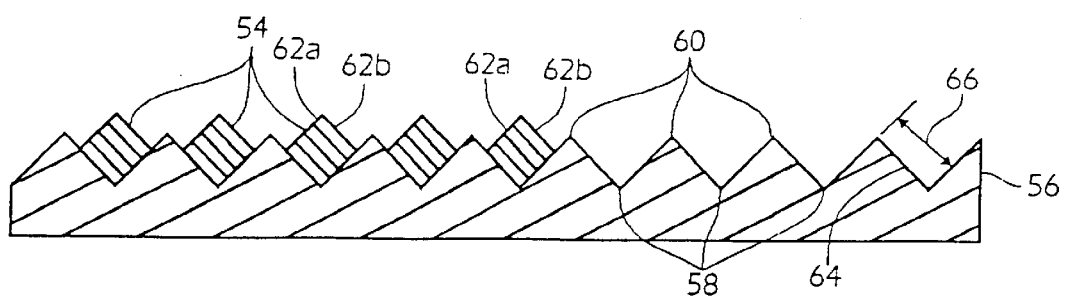

FIGS. 4A and 4B are respective isometric and sectional end views of inspection tray 56, which includes multiple parallel grooves 58 that are separated by parallel ridges 60. Grooves 58 are sized to receive samples 54 and expose two adjacent sides 62a and 62b of each of the samples 54. Inspection tray 56 preferably is formed of nylon and has a color that contrasts with the typical colors of sample 54 (e.g., blue).

Grooves 58 and ridges 60 preferably form cross-sectional angles of about 45° and are sized to accommodate a particular size or range of sizes of french fried potatoes. For example, grooves 58 and ridges 60 have sides 64 with a width 66 of 8 mm (5/16 inch) to accommodate french fried potato stripes with sides 62 having widths 68 of 4.75 to 8 mm (3/16 to 5/16 inch).

Process block 70 indicates that inspection station 12 obtains RGB video signals representing samples 54 in response to control signals from computer system 14. Preferably, video camera 22 obtains two images of samples 54 in inspection chamber 16 under different illumination conditions provided by light source 20 and supplemental light sources 71a and 71b, which preferably are relatively fast-switching incandescent lamps (e.g., halogen). Video camera 22 obtains a generally side illumination image by illuminating sample 54 with illumination sources 20 and 71a. Video camera 22 obtains a generally end illumination image by illuminating sample 54 with illumination sources 20 and 71b. The side and end illumination images of sample 54 cause the ends of french fried potatoes to cast shadows and be identified, whether or not they are aligned with grooves 58. Such separate imaging allows the lengths of the french fried potatoes to be identified regardless of whether they are aligned with grooves 58, thereby providing an enhanced functionality to the present invention. It will be appreciated, however, that a single full-illumination image of sample 54 would be sufficient to obtain basic advantages of the present invention.

Figure 5A:
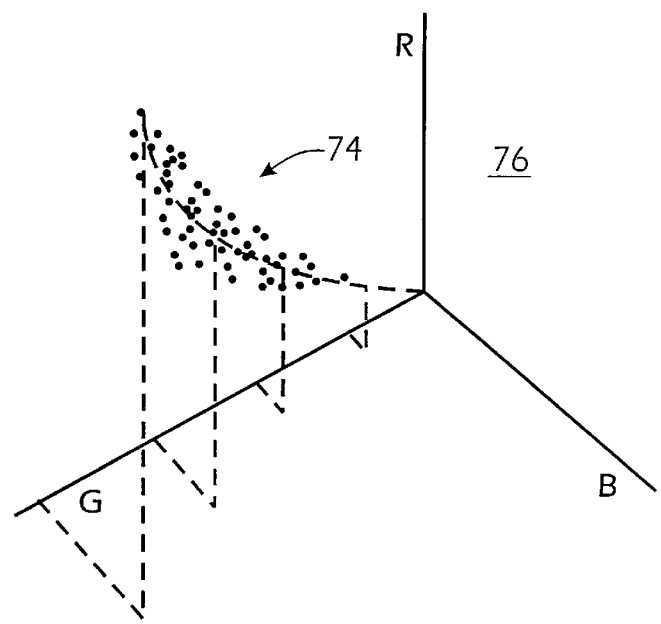
FIGS. 5A–5C are exemplary mappings of pixels in an RGB color space, an HSI color space, and a sample-based color space, respectively.

Process block 72 indicates that computer system 14 converts the RGB video signals from video camera 22 to digitized RGB pixel values that are stored in memory system 26. The conversion is made with a conventional video digitizer or frame grabber (not shown), as is known in the art. The RGB pixel values corresponding to the separate right- and left-side illumination images are stored separately in memory system 26. FIG. 5A shows an exemplary distribution of RGB pixel values 74 in an RGB color space 76 for a simplified right-side illumination image.

Figure 5B:
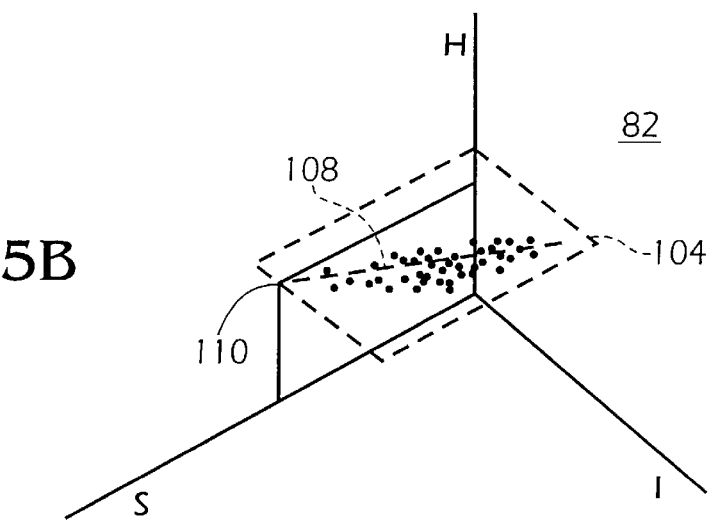
Figure 5C:
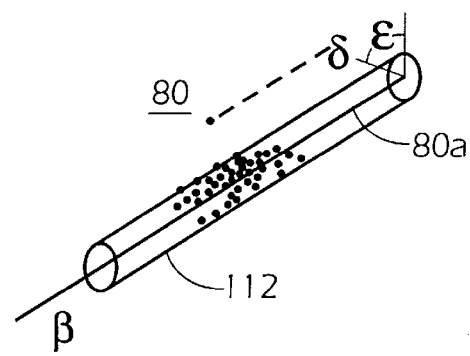

Process block 78 indicates that computer system 14 converts the digitized RGB pixel values corresponding to each of the illumination images from the conventional RGB representation to a sample-based color space 80 (FIG. 5C) in accordance with the present invention. The sample-based color space preferably is based upon a hue-saturation-intensity (HSI) color space 82 (FIG. 5B), as described below in greater detail. Sample-based color space 80 is a cylindrical coordinate system having a linear axis 80a that corresponds to a typical distribution of the overall predominant color or hue of sample 54.

The overall predominant color or hue of sample 54 is based upon the french fried potatoes in the raw, frozen or refried (reconstituted) states. The overall predominant color does not include color deviations, which are described below in greater detail. Moreover, the pixelated manner of operation according to this invention allows the overall predominant color to be determined despite the presence of such deviations in sample 54. Pixel values corresponding to deviations may be omitted automatically from determinations of the overall predominant color. In contrast, conventional color grading systems provide an average reflectance measurement that either incorporates the such deviations into the color determination or requires that articles with such deviations be removed manually from the sample.

Process block 86 indicates that samples 54 are graded according to the positions of the corresponding pixels along linear axis 80a in sample-based color space 80. In this regard, the linear axis functions as a quantified color grading scale analogous to, for example, color standard 000-4 standard for frozen french fried potatoes promulgated by the United States Department of Agriculture (USDA).

Linear axis 80a provides a quantized scale for grading the predominant colors of sample 54. With reference to french fried potatoes, for example, linear scale 80a is represented by the coordinate β and encompasses degrees of browning represented by USDA color standard 000-4. In addition, linear scale 80a provides a significantly greater color resolution, preferably of about 256 levels, that is applied automatically in contrast to the human perception basis of the USDA scale. Sample-based color space 80 further includes an angular coordinate ε that corresponds approximately to color or hue in HSI color space 82 and a radial coordinate δ corresponding to color differences. Coordinates ε and δ provide a perceptually uniform distribution of colors by which color deviations may be identified and characterized.

With respect to french fried potatoes, for example, the color deviations are any blemishes, regardless of origin, including blemishes typically referred to as defect color variations, mottling, sugar ends, sugar tips. Variations refer to french fried potato strips having at least one-third of the imaged surface area (continuous or accumulative) substantially lighter or darker than the predominant overall color of the sample. The terms substantially lighter or darker refer to differences of ½ to 1 USDA color unit from the predominant overall color of the sample, depending on the customer requirements or grade level.

Mottling refers to localized concentrations of reducing sugars that cause intermittent or scattered areas on a french fried potato strip to be ½ USDA color unit darker than the predominant overall color of the sample. The degree of acceptable affected area is dependent upon customer requirements or grade level.

Sugar ends refer to ends of french fried potato strips with 3 USDA color units, or darker, over at least ¼ inch on at least three sides. Sugar tips refer to ends of french fried potato strips with 3 USDA color units, or darker, that do not otherwise meet the definition of sugar ends.

Defects refer to a variety of blemishes that detract from the overall appearance of the french fried potatoes on a strip-by-strip basis. USDA standards are used to define and classify defects into categories such as Critical, Major, Minor, and Insignificant according to sizes and degrees of discoloration. Acceptable levels of defects are determined by customer requirements or grade levels. Defects conventionally are determined while the french fried potatoes are in the frozen, parfried, or raw state.

Figure 6:
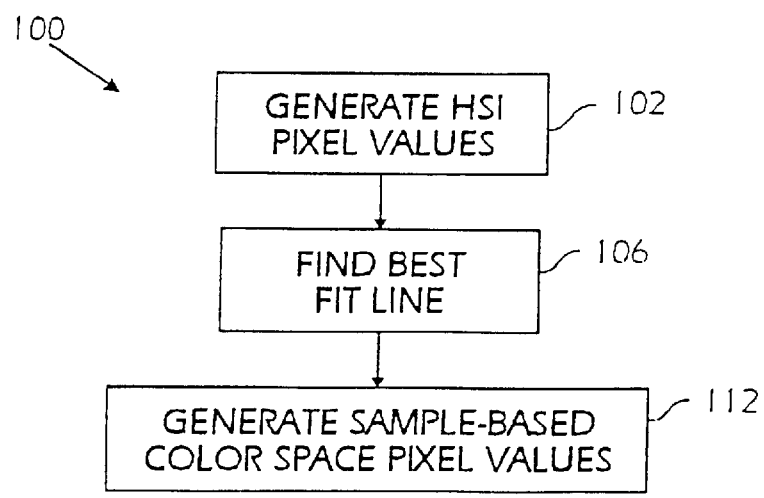
FIG. 6 is a flow diagram of a color space conversion process for converting RGB pixel values to corresponding pixel values in a sample-based color space.

FIG. 6 is a flow diagram of a color space conversion process 100 for converting the digitized RGB pixel values in RGB color space 76 to corresponding pixel values in sample-based color space 80. Color space conversion process 100 is described with reference to FIGS. 5A–5C and frozen french fried potatoes. It will be appreciated, however, that color space conversion process 100 is similarly applicable to samples of like articles having natural color variation, particularly frozen french fried potatoes that have been refried or reconstituted.

Process block 102 indicates that HSI pixel values corresponding to HSI color space 82 are generated from the RGB pixel values obtained in accordance with process block 72. The RGB pixel values in RGB color space 78 for naturally-occurring color variation typically are distributed as a superquadric, which appears "banana-shaped." The corresponding HSI color space values are distributed generally along a surface 104 that preferably is a constant hue value for selected samples such as french fried potatoes. For each RGB pixel value, the corresponding HSI color space value is calculated by the following equations:

$$H = \frac{\pi}{2} - \tan^{-1}\frac{2R - G - B}{\sqrt{3(G - B)}} \text{ for } G < B$$

$$H = \frac{3\pi}{2} - \tan^{-1}\frac{2R - G - B}{\sqrt{3(G - B)}} \text{ for } G > B$$

$$H = 0 \text{ for } G = B$$

$$I = \frac{R + G + B}{3}$$

$$S = 1 - \frac{\min(R, G, B)}{I}$$

Process block 106 indicates that a best fit line 108, preferably a straight line, is generated within surface 104. Line 108 extends through the HSI pixel values and a zero intensity point 110 represented by HSI color space coordinates ($H_0$, $S_0$, 0). The orientation or direction of line 108 is defined by a normalized direction vector $\bar{x}$. For HSI pixel values that are not of a constant hue value, surface 104 may be determined by a conventional least-squares approximation.

Process block 112 indicates that the HSI pixel values are converted to a circular cylindrical sample-based color space 80 in which line 108 forms linear axis 80a. For each point Q=(H', S', I') in HSI color space 82, a corresponding point V=($\beta$, $\delta$, $\epsilon$) in sample-based color space 80 is determined according to the following equations:

$$\beta = ((H', S', I') - (H_0, S_0, 0))\bar{X}$$

$$\delta = |((H', S', I') - (H_0, S_0, 0)) - \beta\bar{X}|$$

$$\epsilon = \cos^{-1}\frac{(\bar{n}_h \times \bar{x}) \cdot (((H', S', I') - (H_0, S_0, 0)) - \beta\bar{X})}{\delta}$$

A normal vector $\bar{n}_h$ to surface 104 preferably is determined by a conventional regression algorithm. All other terms for determining each point V=($\beta$, $\delta$, $\epsilon$) are described above. Table 2 lists simplified sets of exemplary RGB and HSI pixel values corresponding to the pixel values shown in FIGS. 5A and 5B for a sample of french fried potatoes. The RGB pixel values are a digitized form of the RGB video signal obtained by video camera 22, and the HSI pixel values are determined from the RGB pixel values by the equations described with reference to process block 102.

TABLE 2

| Exemplary RGB Color Space Pixel Values | | | Exemplary HSI Color Space Pixel Values | | |
|---|---|---|---|---|---|
| Red | Green | Blue | Hue | Intensity | Saturation |
| 108 | 74 | 26 | 163.62 | 69.33 | 159.38 |
| 119 | 82 | 29 | 163.46 | 76.67 | 158.54 |
| 126 | 86 | 31 | 163.92 | 81 | 157.41 |
| 127 | 89 | 31 | 162.76 | 82.33 | 158.99 |
| 130 | 92 | 40 | 163.97 | 87.33 | 138.21 |
| 130 | 94 | 42 | 163.37 | 88.67 | 134.21 |
| 130 | 96 | 43 | 162.53 | 89.67 | 132.71 |
| 118 | 83 | 29 | 162.65 | 76.67 | 158.54 |
| 125 | 86 | 30 | 163.43 | 80.33 | 159.77 |
| 130 | 94 | 44 | 163.8 | 89.33 | 129.4 |
| 131 | 94 | 44 | 164.11 | 89.67 | 129.87 |
| 112 | 78 | 28 | 163.17 | 72.67 | 156.74 |
| 126 | 88 | 31 | 162.95 | 81.67 | 158.2 |
| 130 | 91 | 36 | 163.63 | 85.67 | 147.84 |
| 129 | 97 | 47 | 162.51 | 91 | 123.3 |

French fried potatoes are characterized by HSI pixel values of a substantially constant hue. As a result, HSI surface 104 corresponds to a plane determined by the average hue value of 163.33 of all the hue pixel values in Table 2. It will be appreciated that for other types of samples that do not have a substantially constant hue value, HSI surface 104 can be determined by a conventional least-square approximation from the HSI pixel values.

Figure 7:
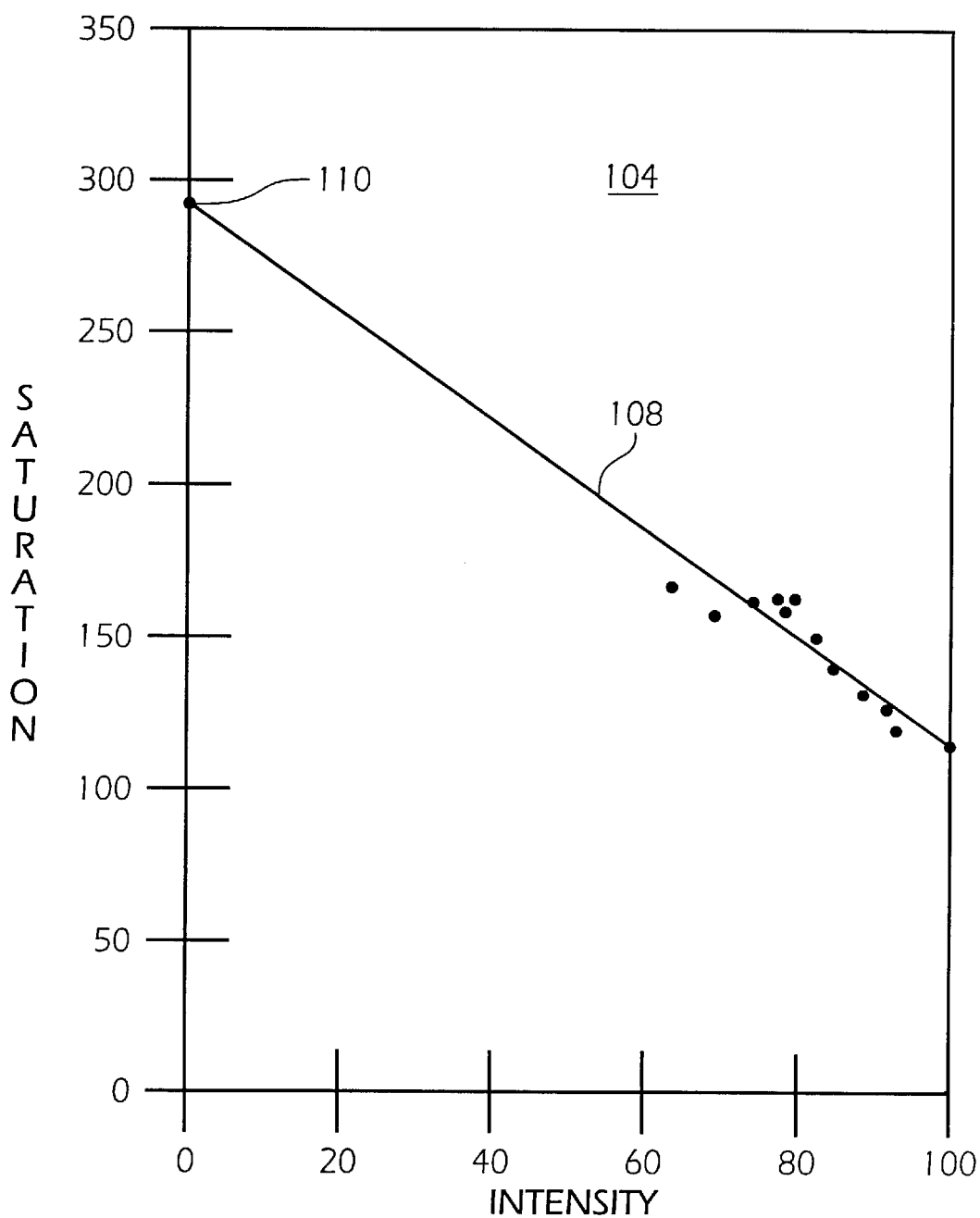
FIG. 7 is a graph representing exemplary pixel values with constant hue in an HSI color space.

FIG. 7 is a graph showing a straight line 108' determined with reference to the HSI pixel values of Table 2 by a conventional linear regression calculation. As described above, straight line 108' extends through a zero intensity point 110'. Exemplary straight line 108' may be represented by the equation:

$$S = -1.746I + 291.4$$

With reference to the slope of straight line 110', normalized direction vector $\bar{x}$ may be represented relative to the origin of the graph of FIG. 7 by the point (0,−0.868, 0.497). The normal vector $\bar{n}_h$ corresponding to surface 104 in the form of a constant value plane is (1, 0, 0). With normalized direction vector $\bar{x}'$, normal vector $\bar{n}_h$, and zero intensity point 110' represented by HSI color space coordinates $(H_0, S_0, 0)=(163.33, 291.4, 0)$, each corresponding point $v=(\beta, \delta, \epsilon)$ in sample-based color space 80 may be calculated. Table 3 lists the corresponding exemplary sample-based color space pixel values, with the angles $\epsilon$ listed in degrees.

TABLE 3

Exemplary Sample-Based Color Space Pixel Values

| β | δ | ε |
|---|---|---|
| 149.05 | 5.44 | 2.893 |
| 153.42 | 0.53 | 164.3 |
| 156.56 | 3.76 | 170.9 |
| 155.84 | 5.68 | 174.3 |
| 176.37 | 0.72 | 62.67 |
| 180.50 | 1.16 | 4.169 |
| 182.30 | 1.31 | 37.81 |
| 153.42 | 0.85 | 127.1 |
| 154.17 | 4.30 | 178.9 |
| 185.0 | 3.01 | 9.027 |
| 184.7 | 2.56 | 17.73 |
| 153.00 | 3.85 | 2.284 |
| 156.20 | 4.70 | 175.4 |
| 167.18 | 3.02 | 174.2 |
| 191.13 | 4.63 | 10.18 |

Analysis of the pixel values in the sample-based color space includes defining a region of acceptable sample colors and, consequently, relative deviations from acceptable colors. With reference to sample-based color space 80, for example, an acceptable color region 112 is defined about axis 80a and forms a generally cylindrical volume. The particular dimensions of acceptable region 112 are selected by a user.

With reference to sample-based color space 80' determined from the exemplary pixel values of Table 2, for example, another exemplary pixel value that is included in acceptable region 112 could be $Q_{RGB}=(125, 87, 41)$, $Q_{HSI}=(165.35, 131.03, 84,33)$, and $V=(181.11, 6.81, 17.23°)$. In particular, the δ value of 6.81 would be considered to be within the δ value of 10 that defines an exemplary acceptable region 112. Accordingly, such an exemplary pixel value would be characterized as a valid or acceptable french fry color. The browning value β of 181.11 could be correlated to a conventional color scale, such as the USDA standard, by a conventional look up table.

Another exemplary pixel value that is not included in acceptable region 112 could be $Q_{RGB}=(180, 100, 70)$, $Q_{HSI}=(177.82, 102.00, 116.67)$, and $V=(222.38, 16.15, -25.32°)$. In particular, the δ value of 16.15 would be considered to be outside the δ value of 10 that defines an exemplary acceptable region 112. Accordingly, such an exemplary pixel value would be characterized a defect or an unacceptable french fry color. The browning value β of 222.38 could be correlated to a conventional color scale, such as the USDA standard, by a conventional look up table. The angle value $\epsilon$ of −25.32° would correspond to a particular discoloration (e.g., light red-grey).

Conventional grading models are based upon certain defect types (e.g., light or dark) and the criticality of defects is determined by certain size thresholds. For example, light and dark defects of, respectively, 5/16 inch and 1/4 inch diameters could be considered major. A disadvantage of such conventional size and color thresholds for grading defects is that they are discontinuous, in contrast to customer perceptions of defects. A dark defect is not perceived to be qualitatively different from a slightly smaller defect of the same color. As a result, defect definitions must be overly inclusive to distinguish different types or sizes of defects. Otherwise acceptable products are therefore wasted as a consequence.

Figure 8A:
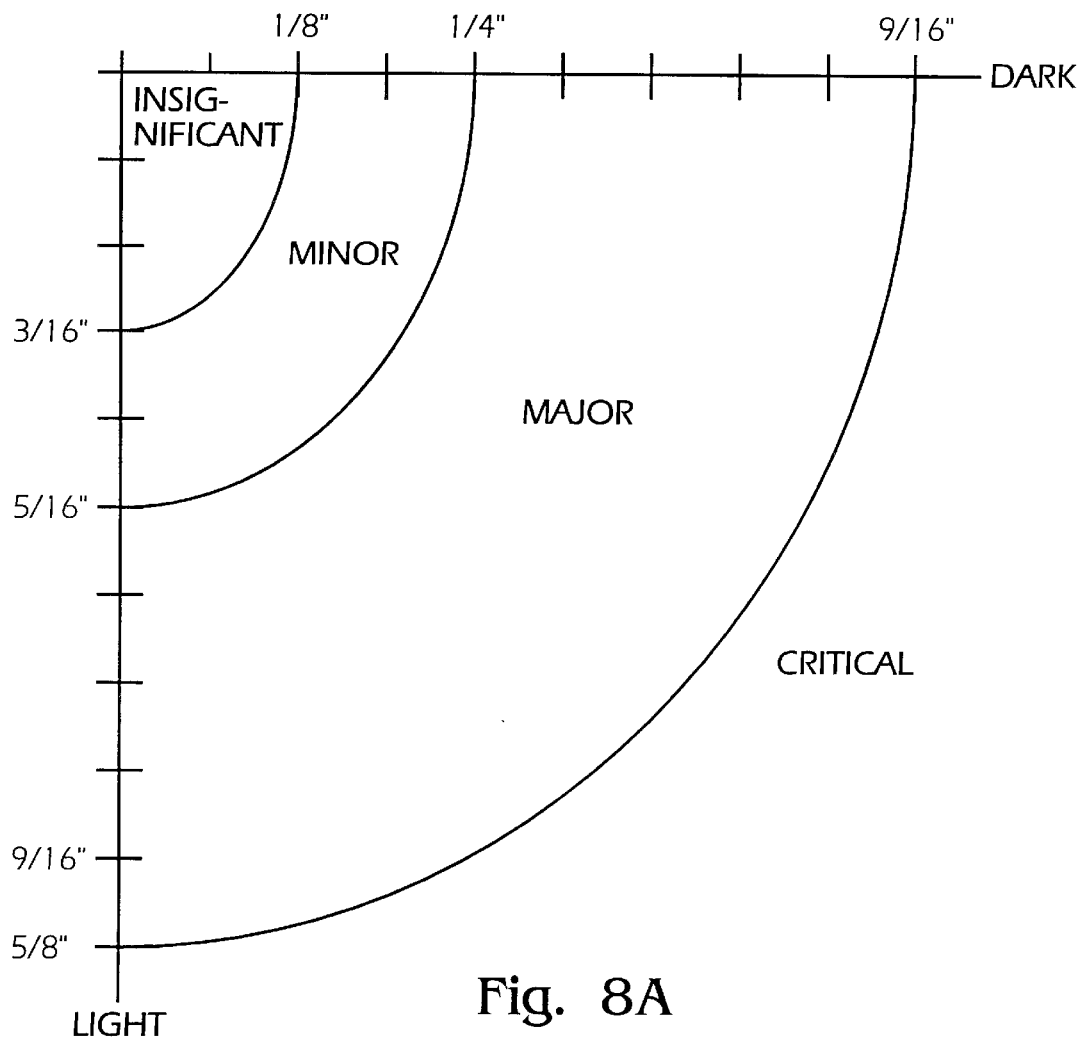
FIG. 8A and 8B are graphical representations of defect characterization thresholds used in accordance with this invention.
Figure 8B:
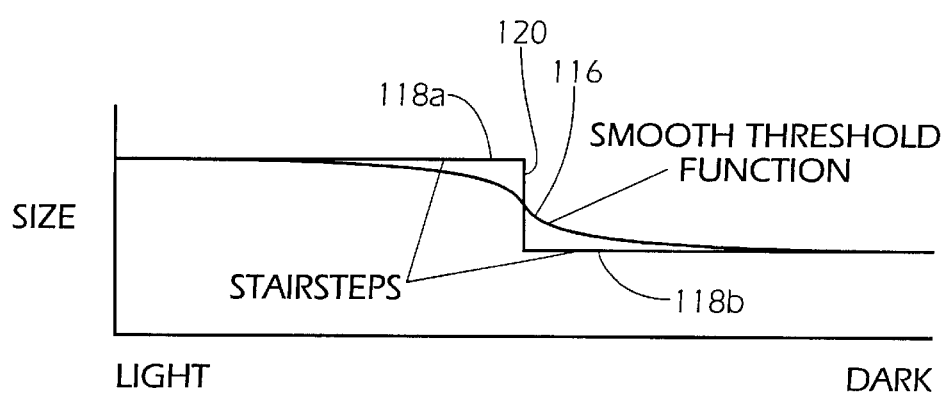

In accordance with this invention, therefore, continuous defect grading is utilized to minimize waste. FIGS. 8A and 8B are graphical representations of defect characterization standards used in accordance with this invention. FIG. 8A shows size-based defect grades for "light" and "dark" defects of different sizes classified as insignificant, minor, major, and critical. Defect sizes are determined as numbers of adjacent pixels having values associated with a particular defect grade. FIG. 8B is a graph showing a continuous transition 116 between color grades 118a and 118b according to this invention. Continuous transition 116 is distinguished from a conventional discontinuous or step transition 120 in which defects of different classes have different threshold colors.

Based upon the optical data obtained according to this invention, defect characterizations can be made based upon actual defect measurements rather than discontinuous threshold definitions. Moreover, it will be appreciated that variations of the type listed in Table 1 above may more accurately measured in the same manner.

Calculation of severity measure for french-fry defects and variations

Another aspect of this invention is a defect severity valuation. The severity is a scalar that describes the overall visual impact of a defect or variation on a french fry. Area and darkness of a group of pixels is combined into one number resulting in a simpler grading scheme than the one currently used. Currently, defects are graded according to darkness and size separately. The technician first decides whether a defect is light or dark. The size limits for defects are dependent on the light/dark decision.

The unscaled severity measure is calculated as the summation of the differences between the darkest allowed color (defect threshold) and the value of a defect pixel (all summations in the following formulas are summations of pixels in a defect area):

$$s = \sum_A (b_0 - b_d)$$

$b_d$ denotes a defective pixel, A is the defect area and $b_0$ is the defect threshold.

The unscaled severity can range from 0 to arbitrarily large numbers for large defect areas. The goal is to calculate a scaled severity that ranges from 0 to a fixed upper limit such as the value 100, which is defined as the severity s of a critical defect based on current grading schemes. The scaled severity is calculated as follows:

$$s = \min\left(100 * \frac{\sum_A (b_0 - b) - \sum_{A_{min}} (b_0 - (b_0 - 1))}{\sum_{A_{crit}} (b_0 - b_1) - \sum_{A_{min}} (b_0 - (b_0 - 1))}, 100\right)$$

-continued $$s = \min\left(100 * \frac{\sum\limits_{A}(b_0 - b) - A_{min}}{\sum\limits_{A_{crit}}(b_0 - b_1) - A_{min}}, 100\right)$$

$A_{crit}$ is the area limit of a critical defect according to current grading rules, $A_{min}$ is the area limit of a light minor defect, $b_1$, is the darkest allowed color of a light defect, b denotes the color of a defective pixel. This formulation provides a severity value s of between 0 and 100, where 0 is the unscaled severity of the least offensive minor light defect and 100 is the severity of the least offensive critical defect. Any severity over 100 is clipped to 100 and the defect is considered critical.

Figure 9:
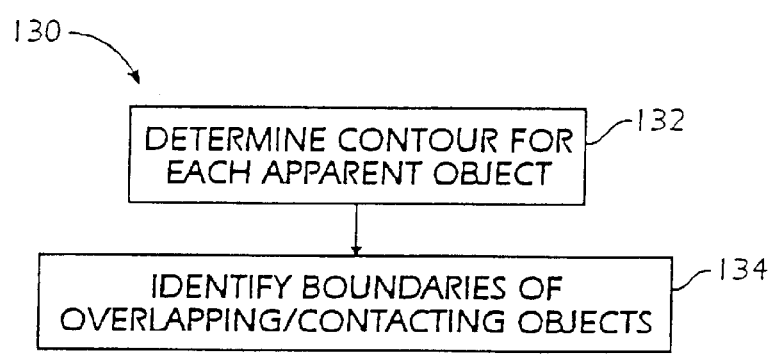
FIG. 9 is a flow diagram showing a process of determining lengths of objects within a sample.

FIG. 9 is a flow diagram of a method 130 of determining lengths and, therefore, distributions of lengths of french fried potatoes in sample 54. This determination requires that the french fried potatoes in sample 54 be distinguished from each other and inspection tray 56. The preferred color (e.g., blue) of inspection tray 56 and the typical colors of sample 54 correspond to distinct pixel values or color coordinates (e.g., RGB or HSI) that are easily discernible by conventional video signal processing techniques.

In contrast, distinguishing the french fried potatoes of sample 54 from each other can require additional processing according to the present invention. In many applications, mechanical singulation or separation of manufactured objects such as french fried potatoes requires either excessive time or complex mechanical apparatus.

Method 130 provides a computer-executed process for distinguishing the video images of the french fried potatoes that are overlapping or contacting each other. Method 130 is performed upon digitized RGB pixel values generated according to process block 72 (FIG. 3) and provides effective singulation or separation of the video images of contacting or overlapping french fried potatoes. For purposes of generalization, each of the french fried potatoes in sample 54 is referred to hereinbelow as an object. The video images of the objects are referred to as apparent objects.

Process block 132 indicates that a boundary or contour is determined for each apparent object in sample 54. The apparent objects include singulated objects and groupings of two or more contacting or overlapping objects. Preferably, a boundary of each apparent object is determined by a conventional eight-neighbor contour follower method.

Process block 134 indicates that boundaries of overlapping or contacting objects are identified by, for example, a Sobel filter applied to saturation color component values generated from the RGB color component values as described above. The conventional Sobel filter includes a pair of masks $S_h$ and $S_v$ adapted for identifying respective horizontal and vertical edges and represented as:

$$S_h = \begin{vmatrix} -1 & -2 & -1 \\ 0 & 0 & 0 \\ 1 & 2 & 1 \end{vmatrix} \quad S_v = \begin{vmatrix} -1 & 0 & 1 \\ -2 & 0 & 2 \\ -1 & 0 & 1 \end{vmatrix}$$

When applied to a pixel $(x_0, y_0)$ having a saturation value $p(x_0, y_0)$ and positioned among pixels $(x_i, y_i)$ having saturation component values represented as $p(x_i, y_i)$, masks $s_h$ and $s_v$, provide by discrete convolution the respective filtered values:

$$M_h = -p(x_{0-1}, y_{0-1}) - 2p(x_0, y_{0-1}) - p(x_{0+1}, y_{0-1}) +$$
$$p(x_{0-1}, y_{0+1}) + 2p(x_0, y_{0+1}) + p(x_{0+1}, y_{0+1})$$
$$M_v = -p(x_{0-1}, y_{0-1}) - 2p(x_{0-1}, y_0) - p(x_{0-1}, y_{0+1}) +$$
$$p(x_{0+1}, y_{0-1}) + 2p(x_{0+1}, y_0) + p(x_{0+1}, y_{0+1})$$

By convention, the origin (i.e., pixel (0,0)) is taken to be the upper left-hand corner of a display.

The Sobel filter magnitude may be determined as the square root of the sum of the squares of the filter values $M_h$ and $M_v$, and the magnitude of the Sobel filter is subjected to a binary threshold filter. Specifically, each pixel is assigned a binary value of 0 or 1 according to whether or not the Sobel filter magnitude is less than a preselected threshold value.

The Sobel filter is capable of identifying pixels of contrasting saturation. Contacting or overlapping objects having generally similar color characteristics frequently will have apparently contrasting saturation characteristics arising from the differing orientations or positions of the objects. Whenever this occurs, the Sobel filter is capable of identifying boundaries of specific objects where they are contacting or overlapping.

Figure 10A:
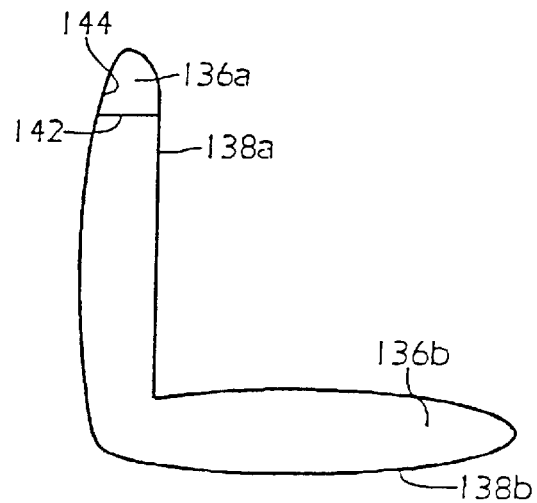
FIGS. 10A–10C are simplified schematic diagrams of objects within a sample for illustrating the process of FIG. 9.
Figure 10B:
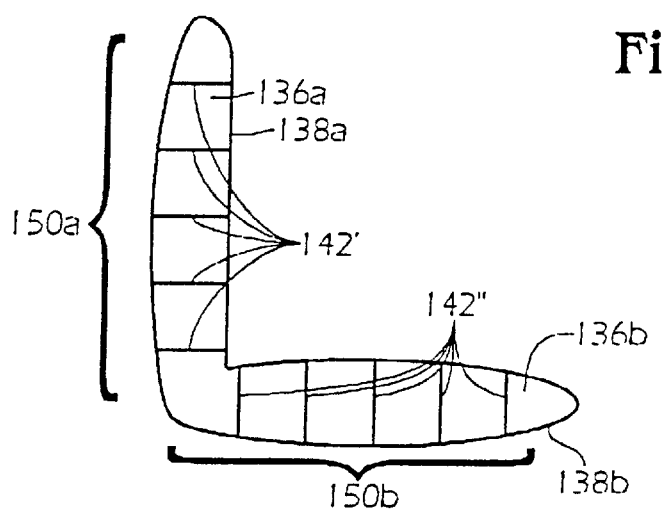
Figure 10C:
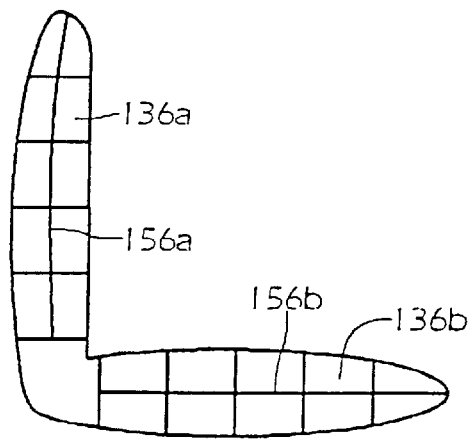

FIGS. 10A–10C are simplified schematic diagrams showing contours of elongated apparent objects 136a and 136b (i.e., video images of french fried potatoes) processed according to this invention. Apparent objects 136a and 136b are shown as contacting each other for purposes of illustration and include contours 138a and 138b formed according to process block 132. Apparent objects 136a and 136b and their contours 138a and 138b are referred to generally by the reference numerals 136 and 138, respectively.

Referring to FIGS. 10A and 10B, process block 140 indicates that transverse segments 142 generally transverse to the longitudinal contours 138 of apparent objects 136 are identified. Referring to FIG. 10A, each transverse segment 142 (only one shown) is formed perpendicular to a baseline 144 that extends between pairs of pixels on contours 138 spaced apart by a predetermined number of successive pixels (e.g., 10). Transverse segments 142 are formed from baselines 144 defined about the entirety of each contour 138. A transverse segment 142 is defined if it intersects its contour 138 within a distance from baseline 144 corresponding to a predetermined maximum allowable thickness of the object.

Process block 146 indicates that the directions of each successive pair of transverse segments 142 are compared to determine whether the transverse segments 142 are parallel with each other to within a predetermined threshold range (e.g., about 20 degree difference). Referring to FIG. 10B, transverse segments 142' in a region 150a of apparent object 136a are deemed to be parallel with each other and associated with object 136a. Transverse segments 142" in a region 150b are deemed to be parallel with each other and associated with object 136b.

Referring to FIG. 10C, process block 154 indicates that midpoints of transverse segments 142 for each of objects 136a and 136b are interconnected to form object center lines 156a and 156b, respectively. Center lines 156a and 156b extend to the approximate ends of objects 136a and 136b identified, for example, as the median pixels on contours 138 between the ends of the nearest transverse segment 142.

Process block 158 indicates that center lines 156a and 156b terminate upon intersecting a contour 138 or another center line 156. Unless identified by the Sobel filter of process block 134, pixels nearest segments 142' and 142" are assigned to respective objects 136a and 136b.

Process block 160 indicates that the lengths of the objects (e.g., french fried potatoes) are determined from the lengths of center lines 156*a* and 156*b*.

Figure 11:
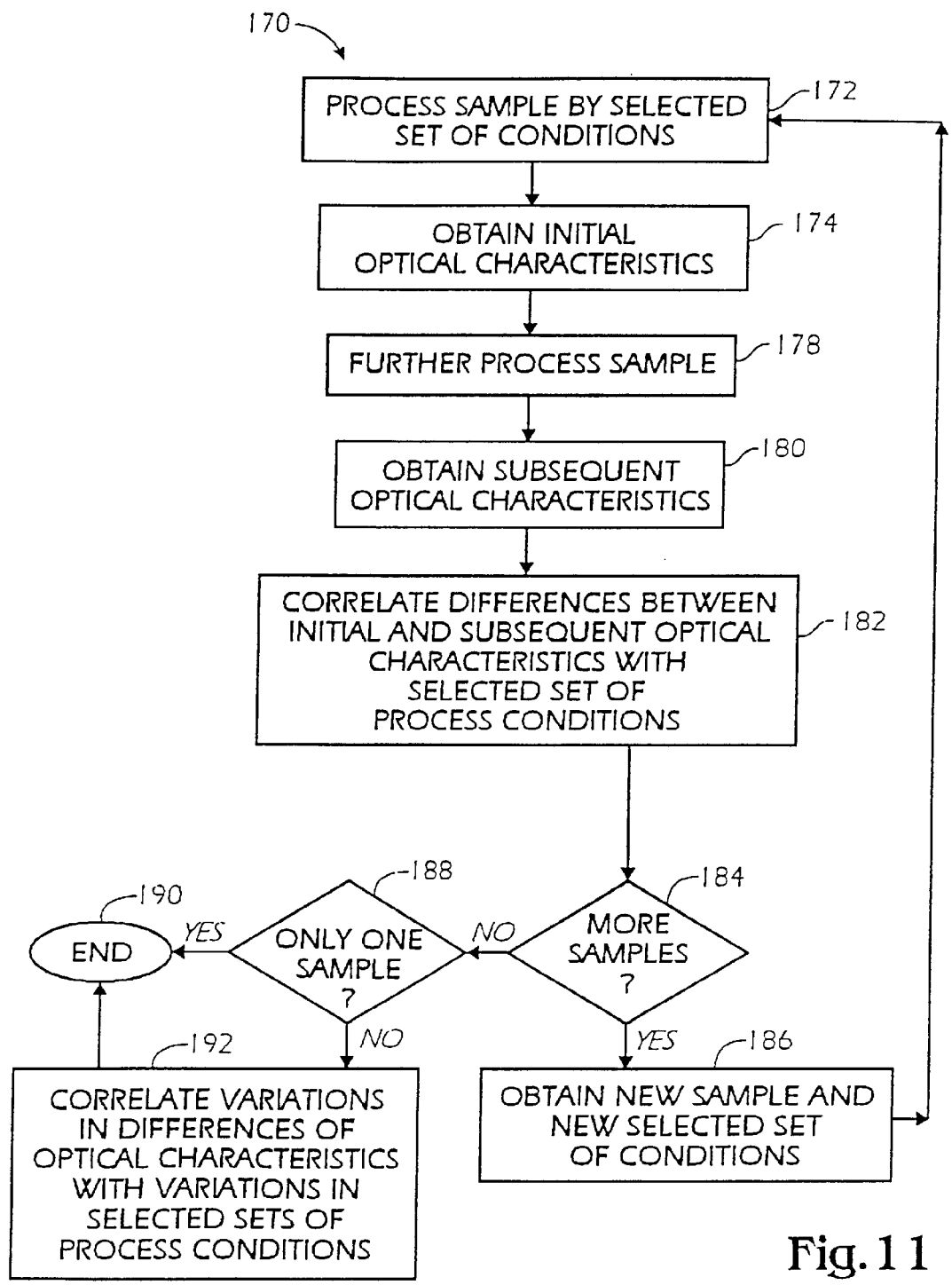
FIG. 11 is a flow diagram showing a grading process for quantifying effects of manufacturing variations.

FIG. 11 is a flow diagram showing a process 170 by which the method of the present invention can be utilized to quantify the effects of various manufacturing changes on the resulting grades or other characteristics of products. As with other aspects of this invention, process 170 is described with reference to french fried potato strips and, particularly, with reference to variations in the parfrying step of manufacturing. It will be appreciated, however, that the process 170 is similarly applicable to determining changes occurring by varying other steps in the manufacture of french fried potato strips, as well as determining changes in other food and non-food products resulting from varying manufacturing steps or processes.

More specifically, process 170 is described with reference to changes in samples 54 of parfried potato strips that are subsequently fried completely. The manufacture or processing of french fried potato strips includes, however, a number of conventional steps such as washing, slicing, blanching, parfrying, freezing, and final frying.

Quantifying the optical characteristics of samples 54 subjected to different processing conditions in these or other steps allows the effects of the different processing conditions to be controlled to provide improved products. Previously, product variations resulting from different processing conditions were qualitatively characterized by manual inspection. Such qualitative characterizations were difficult to correlate with ranges of variations in processing conditions or variations in multiple processing conditions.

Process block 172 indicates that a sample of potato strips is processed (e.g., parfried) according to a selected set of conditions. The selected set of conditions may be those typically used in the manufacture of french fried potato strips or alternative conditions that potentially provide french fried potato strips with improved characteristics.

Process block 174 indicates that a sample of potato strips parfried according to the selected set of conditions is loaded into inspection station 12 and initial optical characteristics of the parfried sample are obtained by optical grading system 10, including length, cut size, and defect data, as described above.

Process block 178 indicates that the parfried sample is removed from inspection station 12 and processed further (e.g., fried). Process block 180 indicates that the sample is returned to inspection station 12 and optical grading system 10, which obtains subsequent optical characteristics relating to the fried sample.

Process block 182 indicates that differences between the parfried and fried samples are determined and correlated with the selected conditions under which the sample was parfried. As one alternative, both types of samples could be correlated with the product as finally prepared for serving.

Decision block 184 represents an inquiry as to whether more samples are to be processed. Decision block 184 proceeds to process block 186 if more samples are to be processed and otherwise proceeds to decision block 188.

Process block 186 indicates that a new sample of potato strips is obtained and new conditions selected for the parfrying of the new sample. Process block 186 returns to process block 172.

Decision block 188 represents an inquiry as to whether only one sample is to be processed. Decision block 188 proceeds to end block 190 if only one sample is to be processed and otherwise proceeds to process block 192.

Process block 192 indicates that variation in the differences between the parfried and fried samples are determined and correlated with variations in the selected conditions under which the samples were parfried.

Having illustrated and described the principles of the present invention of the preferred embodiment, it should be apparent to those skilled in the art that the embodiment can be modified in arrangement and detail without departing from such principles. Accordingly, we claim as our invention all embodiments as come within the scope and spirit and the following claims and equivalents thereto.

We claim:

1. An optical grading method for grading optical characteristics of samples with predominant colors of a substantially common hue, comprising:

obtaining an RGB video signal representing the optical characteristics of the samples with red, green, and blue color component video signals;

generating from the RGB video signal an HSI representation with hue, saturation, and intensity image components;

identifying from the HSI representation the substantially common hue of the predominant colors of the samples;

generating from the HSI representation of the samples a sample-based representation in which the substantially common hue of the predominant colors of the samples forms a grade axis of the sample-based representation; and assigning grades to the samples according to the position along the grade axis;

the RGB video signal including multiple pixels representing the optical characteristics of different portions of the samples and HSI and sample-based representations being generated for each of the pixels;

the multiple pixels of the RGB video signal corresponding predominantly to a surface in the HSI representation and generating the sample-based representation including applying the following equations to each pixel (H', S', I') in the HSI representation:

$$\beta = ((H',S',I') - (H_0,S_0,0))\overline{X}$$
$$\delta = |((H',S',I') - (H_0,S_0,0)) - \beta\overline{X}|$$
$$\epsilon = \cos^{-1}\frac{(\overline{n_h} \times \overline{x}) \cdot (((H',S',I') - (H_0,S_0,0)) - \beta\overline{X}))}{\delta}$$

in which the sample-based representation is represented as a cylindrical coordinate system, $\overline{x}$ represents a normalized direction vector corresponding to a best fit line for the HSI pixel values on the surface in the HSI representation and including a point $(H_0, S_0, 0)$, and $\overline{n}_h$ is a normal vector to the surface in the HSI representation.

* * * * *